(12) United States Patent
Strand et al.

(10) Patent No.: US 11,419,799 B2
(45) Date of Patent: Aug. 23, 2022

(54) ORAL CARE COMPOSITIONS COMPRISING STANNOUS ION SOURCE, NEUTRAL AMINO ACID, AND POLYPHOSPHATE

(71) Applicant: The Procter & Gamble Company, Cincinnati, OH (US)

(72) Inventors: Ross Strand, Singapore (SG); Yunming Shi, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/035,863

(22) Filed: Sep. 29, 2020

(65) Prior Publication Data

US 2021/0093524 A1  Apr. 1, 2021

(51) Int. Cl.
| | |
|---|---|
| *A61K 8/21* | (2006.01) |
| *A61K 8/24* | (2006.01) |
| *A61K 8/25* | (2006.01) |
| *A61K 8/34* | (2006.01) |
| *A61K 8/362* | (2006.01) |
| *A61K 8/365* | (2006.01) |
| *A61K 8/46* | (2006.01) |
| *A61Q 11/00* | (2006.01) |
| *A61K 8/44* | (2006.01) |

(52) U.S. Cl.
CPC .............. *A61K 8/21* (2013.01); *A61K 8/24* (2013.01); *A61K 8/25* (2013.01); *A61K 8/345* (2013.01); *A61K 8/362* (2013.01); *A61K 8/365* (2013.01); *A61K 8/442* (2013.01); *A61K 8/463* (2013.01); *A61Q 11/00* (2013.01); *A61K 2800/28* (2013.01); *A61K 2800/48* (2013.01); *A61K 2800/592* (2013.01); *A61K 2800/92* (2013.01)

(58) Field of Classification Search
CPC ... A61K 8/21; A61K 8/27; A61K 8/19; A61K 2800/592; A61K 8/24; A61K 8/365; A61K 8/43; A61K 8/898; A61K 31/215; A61K 47/183; A61Q 11/00
See application file for complete search history.

(56) References Cited

U.S. PATENT DOCUMENTS

| | | |
|---|---|---|
| 5,281,410 A | 1/1994 | Lukacovic |
| 5,376,360 A | 12/1994 | Domke et al. |
| 10,596,088 B2 | 3/2020 | Strand |
| 10,596,089 B2 | 3/2020 | Strand |
| 10,603,263 B2 | 3/2020 | Strand |
| 2004/0101493 A1 | 5/2004 | Scott et al. |
| 2005/0281758 A1 | 12/2005 | Dodd et al. |
| 2009/0136432 A1 | 5/2009 | Strand et al. |
| 2016/0317409 A1 | 11/2016 | Prencipe et al. |
| 2017/0135935 A1 | 5/2017 | Basa et al. |
| 2019/0117532 A1 | 4/2019 | Strand |
| 2019/0167547 A1* | 6/2019 | Patel ............... A61K 8/86 |
| 2019/0282471 A1 | 9/2019 | Yang et al. |
| 2019/0298620 A1 | 10/2019 | Strand |
| 2020/0146957 A1 | 5/2020 | Strand |
| 2020/0146958 A1 | 5/2020 | Strand |
| 2020/0146959 A1 | 5/2020 | Strand |
| 2021/0093534 A1 | 4/2021 | Strand et al. |

FOREIGN PATENT DOCUMENTS

| | | |
|---|---|---|
| CN | 106937921 A | 7/2017 |
| EP | 2275084 A1 | 1/2011 |
| WO | 2005092277 A1 | 10/2005 |
| WO | 2013034421 A2 | 3/2013 |
| WO | 2015008823 A1 | 1/2015 |

OTHER PUBLICATIONS

International Search Report; International Application No. PCT/CN2019/109425; dated Jul. 6, 2020; 12 pages.
Database GNPD [Online] MINTEL; Apr. 9, 2019 (Apr. 9, 2019), anonymous: "Active Strengthening Fluoride Toothpaste", XP055871 872, Database accession No. 6453945.
Database GNPD MINTEL; Jan. 31, 2018 (Jan. 31, 2018), Anonymous: "Spearmint Toothpaste", XP055871 880, Database accession No. 5414617.
Database GNPD MINTEL; Aug. 7, 2017 (Aug. 7, 2017), anonymous: "Mineral Water & Eucalyptus Toothpaste", XP055871 881, Database Accession No. 5013289.
Database GNPD MINTEL; Mar. 7, 2018 (Mar. 7, 2018), anonymous: "Gel Toothpaste", XP055871 877, Database accession No. 5503447.
International Search Report and Written Opinion; Application Ser. No. PCT/CN2019/109425; dated Dec. 22, 2021, 10 pages.
Scientific Evidence Behind. Advanced Dentifrice Technologies, Jan. 1, 2007, Jan. 1, 2007 (Jan. 1, 2007), pp. 1-164, XP007920425.

* cited by examiner

*Primary Examiner* — Lezah Roberts
(74) *Attorney, Agent, or Firm* — Elizabeth A. Conklin

(57) ABSTRACT

Oral care compositions comprising stannous ion source, neutral amino acid, and polyphosphate are provided for improved efficacy to help inhibit biofilm formation or help disrupt biofilm.

31 Claims, 3 Drawing Sheets

ORAL CARE COMPOSITIONS COMPRISING STANNOUS ION SOURCE, NEUTRAL AMINO ACID, AND POLYPHOSPHATE

FIELD OF THE INVENTION

The present invention relates to oral care compositions comprising stannous ion source, neutral amino acid, and polyphosphate, wherein the concentration of phosphate ion is at least about 10 mMol. Such oral care compositions are useful for improving the delivery of stannous ion to the treated surface and biofilm penetration thereof, while maintaining a pleasant sensorial experience without an associated astringency and metallic taste that ensures product compliance and usage habit to deliver oral health benefits.

BACKGROUND OF THE INVENTION

Dental plaque (also known as dental biofilm) is a sticky, colorless deposit of bacteria that is constantly forming on the tooth surface. Dental plaque is generally made up of bacteria and extracellular polymer substances (so called "EPS"). EPS are biopolymers of microbial origin in which biofilm microorganisms are embedded. *J. Bacteriol.* 2007, 189(22):7945. Saliva, food and fluids combine to produce these deposits that collect where the teeth and gums meet. Plaque buildup is the primary factor in poor oral health that can lead to caries and periodontal (gum) disease, including gingivitis. One way dentifrice compositions help prevent and control plaque is by leveraging anti-bacterial agents; however, the disadvantage and formulation challenge is the unintended reactivity of anti-bacterial agents with formulation ingredients. This may include oxidative degradation, hydrolysis, adsorption or precipitation of oxy-hydroxide species, any of which can impact the bio-availability of the anti-bacterial agent. There is a continuing need to provide such formulations that help prevent plaque formation on teeth and/or minimize the use of antimicrobial agents.

Stannous ion sources, including stannous salts such as stannous fluoride, have been used in oral care compositions as to provide antimicrobial benefits, for example to prevent or eliminate biofilm on teeth. However, there are disadvantages for conventional stannous containing oral care compositions. A first disadvantage routinely encountered during use of effective stannous fluoride formulations is unacceptable formulation astringency. Another disadvantage is formulating stannous ions stably, as the tin (II) ion is both prone to oxidation towards tin (IV) and to precipitate from aqueous solution as stannous hydroxide. Such stannous containing oral care compositions can also exhibit a metallic taste that is undesirable for consumers. Therefore, it is desired to improve stannous-containing oral care compositions to provide antimicrobial benefits and biofilm penetration, while maintaining a pleasant sensorial experience for the consumer, without the typical disadvantages associated with conventional stannous containing oral care compositions.

SUMMARY OF THE INVENTION

The present invention attempts to address this need based, at least in part, on the surprising discovery that the combination of a neutral amino acid (such as, for example, glycine, asparagine, glutamine, or combinations thereof), a stannous ion source, and polyphosphate in an oral care composition provides improvements to inhibit biofilm formation or help disrupt biofilm. In particular, the oral care composition comprises neutral amino acid for gingival wound healing, and stannous ion source as an anti-bacterial agent to combat the undesirable effects of bacteria activity in the oral cavity.

One advantage of the present invention is "better deep biofilm penetration and/or bacteria kill". To this end, it is further surprisingly found that the penetration depth and/or penetration rate of stannous ion into the biofilms may be increased, when used in combination with neutral amino acid and polyphosphate. In short, the combination of neutral amino acid, stannous ion source, and polyphosphate in the oral care composition may be such that an improvement in the Gum Health benefit is achieved. Furthermore, the enhanced penetration of stannous can treat, control, and neutralize the hard to reach anaerobic bacteria and endotoxins such as lipopolysaccharide (LPS).

It is an advantage of the present invention to provide oral care compositions having improved penetration depth of the anti-bacterial agent(s) into the biofilms. It is yet a further advantage of the present invention to provide oral care compositions having improved penetration rate of the anti-bacterial agent(s) into the biofilms. Furthermore, it is surprisingly found that the use of neutral amino acid in the present invention facilitates to achieve improved penetration depth and/or penetration rate of the anti-bacterial agent(s) into the biofilms.

It is yet a further advantage of the present invention to provide cost effective and efficacious oral care compositions for promoting Gum Health. It is yet a further advantage that the oral care composition, is a dentifrice, and preferably provides pleasant taste and mouth-feel experience. It is yet a further advantage that the oral care compositions have physical and chemical stability across a range of manufacturing, handling and storage conditions. It is yet a further advantage that the oral care compositions have a stable quality of end product (e.g., consistent visual appearance and no discoloration, gingival wound healing performance, etc.) even after three months storage at 40° C. To this end, it is surprisingly found that the use of neutral amino acid helps to achieve such stable quality of end product, better than basic amino acid (e.g. lysine). It is yet a still further advantage that the oral care compositions of the present invention minimize the use of anti-bacterial agents. It is yet a still further advantage that the oral compositions of the present invention minimize the amount of the neutral amino acid to reduce and/or eliminate the instability and/or discoloration problems as described above.

In one aspect, the present invention is directed to a composition comprising a stannous ion source, a neutral amino acid, and polyphosphate. Preferably the composition is an oral care composition. More preferably, the composition comprising: a) from about 0.01% to about 5%, preferably from about 0.05% to about 4%, by weight of the composition, of a stannous ion source; and b) from about 0.01% to about 10%, preferably about 0.05% to about 5%, by weight of the composition, of a neutral amino acid. Preferably, the neutral amino acid is selected from the group consisting of alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, salts thereof, and combinations thereof; more preferably, the neutral amino acid is selected from the group consisting of glycine, asparagine, glutamine, salts thereof, and combinations thereof.

In another aspect of the present invention, a method is provided for promoting Gum Health in a subject comprising administering to the subject's oral cavity an oral care composition of the present invention.

In yet another aspect of the present invention, there is provided a use of neutral amino acid for making an oral care composition for promoting Gum Health in a subject.

These and other features of the present invention will become apparent to one skilled in the art upon review of the following detailed description when taken in conjunction with the appended claims.

DETAILED DESCRIPTION OF THE INVENTION

Definitions

Figure 1:
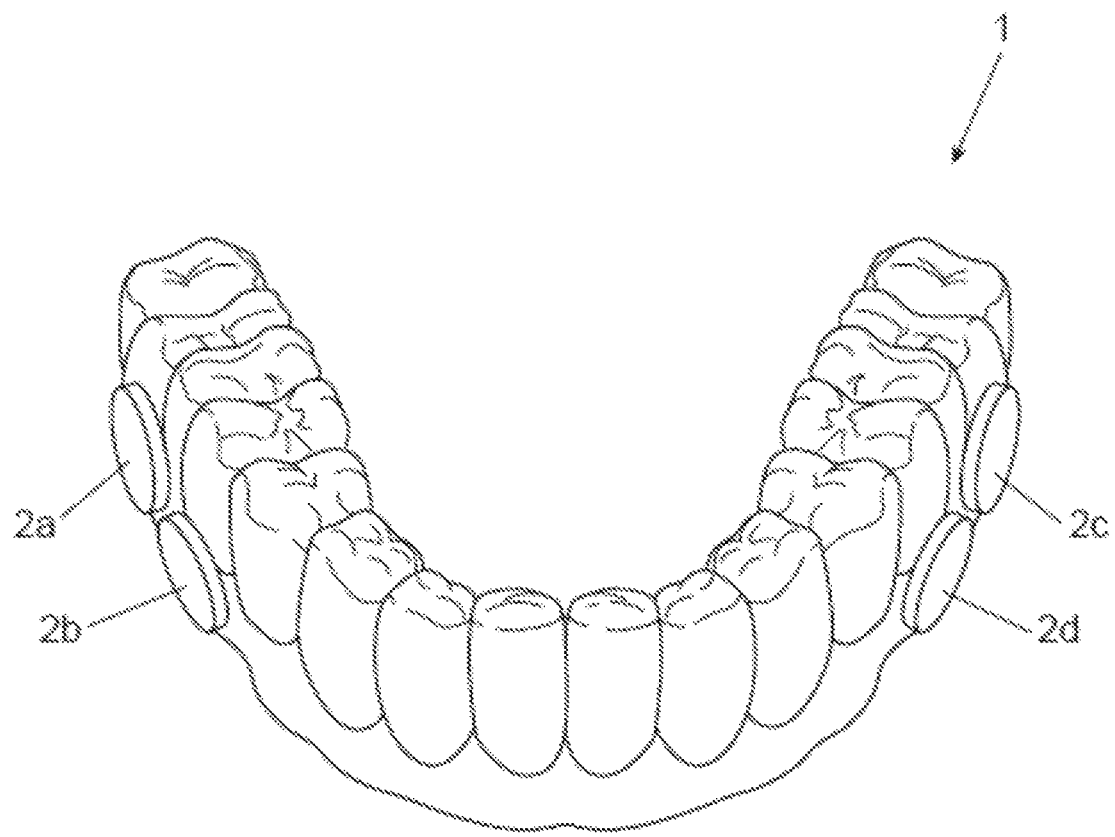
FIG. 1 is a perspective view of an oral splint with Hydroxyapatite ("HA') disks attached thereto.

As used herein, the articles including "a" and "an" when used in a claim, are understood to mean one or more of what is claimed or described.

The terms "alleviate" and "alleviating" are used interchangeably and means minimizing, preventing, delaying, and/or treating at least one symptom of gum disease to effect positive change (i.e., benefit) to the user.

The term "biofilms" as used herein means a matrix-enclosed bacterial population adherent to each other and/or to surfaces or interfaces in the oral cavity.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "dentifrice" as used herein means paste, gel, powder, tablets, or liquid formulations, unless otherwise specified, that are used to clean the surfaces of the oral cavity.

The term "Gum Care" as used herein refers to inherent or promoted benefits of an oral care composition directed, principally, to alleviating one or more symptoms associated with an early stage of gum disease (i.e., gingivitis). Such symptoms may include, for example bleeding gums; and red, swollen, or tender gums.

The term "Gum Health" as used herein refers to inherent or promoted benefits of an oral care composition to provide "Gum Care" benefits that include at least improve gingival wound healing, as well as, providing additional improve reduction of bacterial activity to mitigate the harmful effects of bacteria as it relates to gum disease, including gingivitis, periodontitis or both.

The term "oral care composition" or "oral care compositions" as used herein means a product that in the ordinary course of usage is retained in the oral cavity for a time sufficient to contact some or all of the dental surfaces and/or oral tissues for purposes of oral activity. In one aspect, the composition provides a gum care benefit when used in the oral cavity. The oral care composition of the present invention may be in various forms including toothpaste, dentifrice, tooth gel, tooth powders, tablets, rinse, mouthwash, sub gingival gel, foam, mouse, chewing gum, lipstick, sponge, floss, prophy paste, petrolatum gel, denture adhesive, or denture product. In one aspect, the oral composition is in the form of a paste or gel. In another aspect, the oral composition is in the form of a dentifrice. The oral composition may also be incorporated onto strips or films for direct application or attachment to oral surfaces, or incorporated into floss.

The term "amino acid", "neutral amino acid" used herein the present invention refers to the amino acid including both in free form and salts form.

The term "partially water soluble" as used herein means a compound has a solubility of 1 g/1000 ml or more at 25° C.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one aspect, "effective amount" means at least 0.01% of the material, by weight of the composition, alternatively at least 0.1%.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "promoting" as used herein means to promote and/or enhance the Gum Health benefits associated with using the oral care compositions of the present invention in the oral cavity.

The term "substantially free" as used herein refers to no intentional amount of that material is added to the composition or an amount of a material that is less than 0.05%, 0.01%, or 0.001% of the composition. The term "essentially free" as used herein means that the indicated material is not deliberately added to the composition, or preferably not present at analytically detectable levels. It is meant to include compositions whereby the indicated material is present only as an impurity of one of the other materials deliberately added. The term "free" as used herein refers to no reasonably detectable amount of that material is present in the composition.

The term "synergistic Gum Health benefit" as used herein means analytically measurable increases in any two Gum Health benefits that include at least improve gingival wound healing and improve reduction of bacterial activity in the oral cavity, that is more than additive.

The term "teeth" as used herein refers to natural teeth as well as artificial teeth or dental prosthesis.

The term "total water content" as used herein means both free water and water that is bound by other ingredients in the oral care composition.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

All measurements referred to herein are made at 25° C. (i.e., room temperature) unless otherwise specified.

Oral Care Compositions

It has been surprisingly discovered that the combination of stannous ion (i.e., an anti-bacterial agent), a neutral amino acid (e.g., glutamine, asparagine, or glycine, or salts thereof), and polyphosphate in an oral care composition is particularly useful for promoting Gum Health benefits to users. In particular, the surprising discovery was that the penetration of the stannous ion into the biofilms is markedly improved when combined with the neutral amino acid. Without wishing to be bound by theory, the neutral amino acid contains both carboxylic and amine groups. It is believed that the stannous ions can bind strongly to these chemical moieties on amino acid to positively influence the penetration of stannous ions into the biofilms.

It has also been surprisingly found that the penetration depth and/or the penetration rate of stannous ions into the biofilms may be increased, or markedly increased, when formulated with neutral amino acid. In short, the presence of neutral amino acid in combination with stannous ion source in an oral care composition aids the composition's efficacy in mediating the harmful effects of the bacteria in the biofilms on the gums.

In one aspect, the present invention is directed to an oral care composition comprising: a) from about 0.01% to about 5%, preferably from about 0.05% to about 4%, more preferably from about 0.1% to about 2%, by weight of the composition, of a stannous ion source; b) from about 0.01% to about 10%, preferably from about 0.05% to about 5%, more preferably from about 0.1% to about 2%, by weight of the composition, of a neutral amino acid, and c) polyphosphate, wherein the concentration of phosphate ion is greater than about 10 mMol.

Stannous Ion Source

The present invention relates to the above mentioned oral care compositions comprising a stannous ion source present in the amount of from about 0.01% to about 5%, preferably from about 0.05% to about 4%, or more preferably from about 0.1% to about 2%, by weight of the composition, to provide anti-bacterial effectiveness. The stannous ion source used herein may include any safe and effective stannous salt. Suitable examples of stannous ion source are selected from the group consisting of stannous chloride, stannous fluoride, stannous acetate, stannous gluconate, stannous oxalate, stannous sulfate, stannous lactate, stannous tartrate, stannous iodide, stannous chlorofluoride, stannous hexafluorozirconate, stannous citrate, stannous malate, stannous glycinate, stannous carbonate, stannous phosphate, stannous pyrophosphate, stannous metaphosphate, and combinations thereof. Preferably, the stannous ion source is selected from stannous fluoride, stannous chloride, and combinations thereof. In one preferred aspect, the stannous ion source comprises stannous chloride. In another preferred aspect, the stannous ion source comprises stannous fluoride.

Neutral Amino Acids

The oral care compositions of the present invention comprise a neutral amino acid.

The term "neutral amino acids" as used herein include not only naturally occurring neutral amino acids, such as alanine, asparagine, cysteine, glutamine, glycine, isoleucine, leucine, methionine, phenylalanine, proline, serine, threonine, tryptophan, tyrosine, valine, but also biologically acceptable amino acid which has an isoelectric point in range of pH 5.0 to 7.0. The biologically preferred acceptable neutral amino acid has a single amino group and carboxyl group in the molecule or a functional derivative hereof, such as functional derivatives having an altered side chain albeit similar or substantially similar physio chemical properties. In a further embodiment the amino acid would be at minimum partially water soluble and provide a pH of less than 7 in an aqueous solution of 1 g/1000 ml at 25° C.

Accordingly, neutral amino acids suitable for use in the invention include, but are not limited to, alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, salts thereof, or mixtures thereof. Preferably, neutral amino acids used in the composition of the present invention may include asparagine, glutamine, glycine, salts thereof, or mixtures thereof. The neutral amino acids may have an isoelectric point of 5.0, or 5.1, or 5.2, or 5.3, or 5.4, or 5.5, or 5.6, or 5.7, or 5.8, or 5.9, or 6.0, or 6.1, or 6.2, or 6.3, or 6.4, or 6.5, or 6.6, or 6.7, or 6.8, or 6.9, or 7.0, in an aqueous solution at 25° C. Preferably, the neutral amino acid is selected from asparagine, glutamine, or glycine, more preferably in its free form. If the neutral amino acid is in its salt form, suitable salts include salts known in the art to be pharmaceutically acceptable salts considered to be physiologically acceptable in the amounts and concentrations provided. Preferably the neutral amino acid is present in the amount of from about 0.01% to about 10%, preferably from about 0.05% to about 5%, preferably from about 0.1% to about 3%, preferably from about 0.5% to about 3%, preferably from about 1% to about 3%, by weight of the composition. In one aspect, the neutral amino acid is glutamine (or salt thereof). In another aspect, the neutral amino acid is asparagine (or salt thereof). In yet another aspect, the neutral amino acid is glycine (or salt thereof).

It has been discovered that the above-mentioned stability and discoloration problems can be resolved by adjusting the neutral amino acid concentration in the compositions. Surprisingly, the reduced levels of neutral amino acid (e.g. 2% vs. 8%) do not negatively impact its activity and/or efficacy for gingival wound healing due to the effect, potentially synergistic effect, of combining it with stannous ions in preferred oral care compositions of the present invention. Without wishing to be bound by theory, it is believed that stannous ions can bind strongly to these chemical moieties on the amino acid to positively influence the penetration to maintain sufficient efficacy at lower concentrations.

It has been surprisingly discovered that, the use of neutral amino acid together with stannous provides the end oral care product a stable quality (e.g., consistent visual appearance and no discoloration), compared with using basic amino acid (e.g. lysine). Without wishing to be bound by theory, neutral amino acid generally has less amino group in the molecule than a basic amino acid, thus will reduce the reacting activity of amino group with sugars (e.g. sorbitol), which is believed a reason causing the undesirable browning of an oral care composition (e.g. a dentifrice) over time.

Furthermore, the introductions of amino acid provide gingival would healing benefit and thus be able to minimize the use of other anti-bleeding agents, for example tranexamic acid, epsilon aminocaproic acid, and p-aminomethylbenzoic acid. In some preferred aspects, the oral care composition of the present invention is substantially free of, preferably essentially free of, and more preferably free of, tranexamic acid, epsilon aminocaproic acid, and p-aminomethylbenzoic acid.

In one aspect, the neutral amino acid is uncomplexed. In one aspect, the neutral amino acid is not complexed with zinc.

Polyphosphates

The oral care composition of the present invention further comprises a polyphosphate. The polyphosphate can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present. The polyphosphate can therefore be linear or cyclic (e.g. phytic acid).

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. Alkali earth metal cations, such as calcium, are not preferred because they tend to form insoluble fluoride salts from aqueous solutions comprising a fluoride ions and alkali earth metal cations. Thus, the oral care compositions disclosed herein can be free of or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), or hexametaphosphate (n=21, which is also known as Glass H). Polyphosphates can include those polyphosphate compounds manufactured by FMC Corporation, ICL Performance Products, and/or Astaris. Other suitable polyphosphates are cyclic polyphosphates, such as phytic acid.

Preferably, the type of polyphosphate and the level of polyphosphate incorporated in the oral care composition of the present invention is selected so that the concentration of the phosphate ion is greater than 10 mMol, preferably from about 10 mMol to about 200 mMol, preferably from about 10 mMol to about 150 mMol.

The oral care composition can comprise from about 0.01% to about 25%, from about 0.1% to about 20%, from about 0.5% to about 15%, from about 1 to about 15%, or less than about 10%, by weight of the oral care composition, of the polyphosphate.

In one aspect, the oral care composition comprises less than 12.75%, by weight of the oral care composition, of polyphosphate.

In one aspect, the oral care composition comprises greater than 13.25% by weight of the oral care composition, of polyphosphate.

In one aspect, the polyphosphate is selected from the group consisting of pyrophosphate, tripolyphosphate, hexametaphosphate, and mixtures thereof. Preferably, the polyphosphate is selected from the group consisting of pyrophosphate, tripolyphosphate, and mixtures thereof.

Zinc Ion Source

Optionally, but preferably, the oral care composition may further comprise from about 0.1% to about 5%, preferably from about 0.2% to about 2%, by weight of the composition, of a zinc ion source. Preferably, the zinc ion source is selected from the group consisting of zinc citrate, zinc chloride, zinc sulfate, zinc gluconate, zinc lactate, zinc phosphate, zinc oxide, zinc carbonate, and combinations thereof. More preferably, the zinc ion source is selected from zinc citrate, zinc gluconate, zinc lactate, and combinations thereof.

Alternatively, the oral care composition may comprise a source of zinc ions sufficient to provide from about 0.1% to about 1.5%, preferably from about 0.15% to about 1%, or more preferably from about 0.2% to about 0.55%, by weight of the composition, of zinc ion. Insoluble or sparingly soluble zinc compounds, such as zinc oxide or zinc carbonate, can be used as the zinc source. Preferred zinc sources however are soluble zinc sources such as zinc chloride or zinc sulfate. More preferred zinc sources are those where the zinc is already combined with a suitable chelating agent in the form of a salt or other complex, such as zinc citrate, zinc gluconate, zinc lactate and zinc glycinate. Especially preferred sources of zinc ions are zinc citrate, zinc gluconate, zinc lactate, and combinations thereof.

The oral care compositions of the present invention may optionally also include other anti-bacterial agents, preferably present in an amount of from about 0.035% or more, from about 0.05% to about 2%, from about 0.1% to about 1%, by weight of the composition. Examples of these other anti-bacterial agents may include non-cationic anti-bacterial agents such as, for example, halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilidies. Other useful anti-bacterial agents are enzymes, including endoglycosidase, papain, dextranase, mutanase, and combinations thereof. In another aspect, the other anti-bacterial agent can include triclosan (5-chloro-2-(2,4-dichlorophenoxy)phenol).

Thickening Agent

The oral care compositions of the present invention may optionally comprise a thickening agent. Preferably the oral care composition comprises from about 0.01% to about 10%, preferably from about 0.5% to about 8%, preferably from about 1% to about 5%, preferably from about 1% to about 3%, by weight of the composition, of the thickening agent.

Preferably the thickening agent comprises a thickening polymer, a thickening silica, or a combination thereof. Yet more preferably, when the thickening agent comprises a thickening polymer, the thickening polymer is selected from a charged carboxymethyl cellulose, a non-ionic cellulose derivative, a linear sulfated polysaccharide, a natural gum, polymers comprising at least a polycarboxylated ethylene backbone, and combinations thereof.

In one aspect the thickening silica is obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167).

Preferably the linear sulfated polysaccharide is a carrageenan (also known as carrageenin). Examples of carrageenan include Kappa-carrageenan, Iota-carrageenan, Lambda-carrageenan, and combinations thereof.

In one aspect the CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A).

Preferably a natural gum is selected from the group consisting of gum karaya, gum arabic (also known as acacia gum), gum tragacanth, xanthan gum, and combination thereof. More preferably the natural gum is xanthan gum. Xanthan gum is a polysaccharide secreted by the bacterium *Xanthomonas camestris*. Generally, xanthan gum is composed of a pentasaccharide repeat units, comprising glucose, mannose, and glucuronic acid in a molar ratio of 2:2:1, respectively. The chemical formula (of the monomer) is $C_{35}H_{49}O_{29}$. In one aspect, the xanthan gum is from CP Kelco Inc (Okmulgee, US).

Preferably, the non-ionic cellulose or derivative thereof has an average molecular weight range of about 50,000 to about 1,300,000 Daltons, and preferably an average degree of polymerization from about 300 to about 4,800. More preferably, the non-ionic cellulose or derivative thereof is hydroxyethyl cellulose ("HEC").

Preferably the polymer comprising at least a polycarboxylated ethylene backbone is selected from the group consisting of: co-polymers of maleic anhydride with methyl vinyl ether having a molecular weight of about 30,000 to about 1,000,000 Daltons; homo-polymers of acrylic acid; and co-polymers of maleic acid and acrylic acid or methacrylic.

The co-polymers of maleic anhydride with methyl vinyl ether are at least one of: Gantrez AN139 (M.W. 500,000 daltons), Gantrez AN119 (M.W. 250,000 daltons), or S-97 Pharmaceutical Grade (M.W. 70,000 daltons); and the homo-polymers of acrylic acid and co-polymers of maleic acid and acrylic acid or methacrylic acid are at least one of: Acusol 445, Acusol 445N, Accusol 531, Acusol 463, Acusol 448, Acusol 460, Acusol 465, Acusol 490, Sokalan CP5, Sokalan CP7, Sokalan CP45, or Sokalan CP12S; and (v) combinations thereof.

In an aspect, the GANTREZ™ series of polymers are co-polymers of maleic anhydride with methyl vinyl ether having a molecular weight (M.W.) of 30,000 daltons to 1,000,000 daltons. These co-polymers are available for example as GANTREZ™ AN139 (M.W. 500,000 daltons), AN119 (M.W. 250,000 daltons) and S-97 Pharmaceutical Grade (M.W. 70,000 daltons), from Ashland Chemicals (Kentucky, USA).

In another aspect, the ACUSOL™ and the SOKALAN series of polymers include homopolymers of acrylic acid and copolymers of maleic acid and acrylic acid or methacrylic. Examples are 0:1000 to 1000:0 copolymers of maleic acid with acrylic acid having a molecular weight (M.W.) of about 2,000 to about 1,000,000. These copolymers are commercially available as ACUSOL™ 445 and 445N, ACUSOL™ 531, ACUSOL™ 463, ACUSOL™ 448, ACUSOL™ 460, ACUSOL™ 465, ACUSOL™ 497, ACUSOL™ 490 from Dow Chemicals (Michigan, USA) and as Sokalan® CP 5, Sokalan® CP 7, Sokalan® CP 45, and Sokalan® CP 12 S from BASF (New Jersey, USA).

In another aspect, the crosslinked polyacrylic acid (PAA) polymer is a generic term for the synthetic high molecular weight polymers of acrylic acid. These may be homopolymers of acrylic acid, crosslinked with an allyl ether pentaerythritol, allyl ether of sucrose or allyl ether of propylene. And, in a water solution at neutral pH, PAA is an anionic polymer, i.e. many of the side chains of PAA will lose their protons and acquire a negative charge. Carbopol®-type polymers, such as Carbopol®, Pemulen® and Noveon®, are polymers of acrylic acid, crosslinked with polyalkenyl ethers or divinyl glycol. Carbomer commercial codes, e.g. 940™, indicate the molecular weight and the specific components of the polymer.

Anti-Caries Agent

Optionally, but preferably, the oral care compositions may include an effective amount of an anti-caries agent. In one aspect, the anti-caries agent is a fluoride ion source. Suitable examples of fluoride ions may be selected from a source comprising stannous fluoride, sodium fluoride, potassium fluoride, sodium monofluorophosphate ("MFP"), indium fluoride, amine fluoride, zinc fluoride, and mixtures thereof. Preferably, the fluoride ion source is selected from sodium fluoride, stannous fluoride, MFP, or combinations thereof. The fluoride ion source may be present in an amount of from about 0.0025% to about 10%, or from about 0.05% to about 4%, or from about 0.1% to about 2%, or preferably from about 0.2% to about 1.5%, by weight of the composition, to provide anti-caries effectiveness. In certain aspects, the fluoride ion source can be present in an amount sufficient to provide fluoride ions concentration in the composition at levels from about 25 ppm to about 25,000 ppm, generally at least from about 500 ppm to about 1600 ppm, for example 1100 ppm or 1450 ppm. The appropriate level of fluoride will depend on the particular application. A toothpaste for general user would typically have about 1000 to about 1500 ppm, with pediatric toothpaste having somewhat less.

In some aspects, the fluoride ion source (e.g. anti-caries agent) and the stannous ion source are the same material, for example, stannous fluoride.

pH

The pH of the oral care composition of the present invention may be from about 4.5 to about 11, preferably from about 5 to about 10. In some preferred aspects, the pH of the oral care compositions may be from about 5 to about 7.2. Alternatively, the oral care composition may have a pH of from about 5 to about 9, or from about 5.5 to about 8.5. In some aspects, the pH is from 5.0 to 7.0, alternatively from pH 5.5 to less than pH 7.0, e.g., pH 6.9, or pH 6.8, or pH 6.7, or pH 6.6, or pH 6.5, or pH 6.4, or pH 6.3, or pH 6.2, or pH 6.2, or pH 6.1, or pH 6.0, or pH 5.9, or pH 5.8, or pH 5.7, or pH 5.6, or pH 5.5.

The pH is typically measured using a ratio of 1:3 of paste:water, whereby 1 gram of the oral care composition (e.g., toothpaste) is mixed into 3 grams of deionized water, and then the pH is assessed with an industry accepted pH probe that is calibrated under ambient conditions. The pH is measured by a pH meter with Automatic Temperature Compensating (ATC) probe. For purposes of clarification, although the analytical method describes testing the oral care composition when freshly prepared, for purposes of claiming the present invention, the pH may be taken at any time during the product's reasonable lifecycle (including but not limited to the time the product is purchased from a store and brought to the user's home).

After each usage the electrode should be washed free from the sample solution with water. Remove any excess water by wiping with a tissue, such as Kimwipes or equivalent. When electrode is not in use, keep electrode tip immersed in pH 7 buffer solution or electrode storage solution. Equipment details are as follows:

pH Meter: Meter capable of reading to 0.01 or 0.001 pH units.

Electrode: Orion Ross Sure-Flow combination: Glass body—VWR #34104-834/Orion #8172BN or VWR #10010-772/Orion #8172BNWP.

Epoxy body—VWR #34104-830/Orion #8165BN or VWR #10010-770/Orion #8165BNWP.

Semi-micro, epoxy body—VWR #34104-837/Orion #8175BN or VWR #10010-774/Orion #3175BNWP.

Orion PerpHect combination: VWR #34104-843/Orion #8203BN semi-micro, glass body.

ATC Probe: Fisher Scientific, Cat. #13-620-16.

pH Modifying Agent

The oral care compositions herein may optionally include an effective amount of a pH modifying agent, e.g. wherein the pH modifying agent is a pH buffering agent. The pH modifying agents, as used herein, refer to agents that can be used to adjust the pH of the oral care compositions to the above-identified pH range. The pH modifying agents include hydrochloric acid, alkali metal hydroxides, ammonium hydroxide, organic ammonium compounds, carbonates, sesquicarbonates, borates, silicates, phosphates, imidazole, or mixtures thereof.

Specific pH modifying agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, sodium gluconate, lactic acid, sodium lactate, citric acid, sodium citrate, phosphoric acid, or mixtures thereof.

In one aspect, the oral care composition comprises from about 0.01% to about 3%, preferably from about 0.1% to about 1%, by weight of the composition, of TSP, and from about 0.001% to about 2%, preferably from about 0.01% to about 0.3%, by weight of the composition, of monosodium phosphate. Without wishing to be bound by theory, TSP and monosodium phosphate may have calcium ion chelating activity and therefore provide some monofluorophosphate stabilization (in those formulations containing monofluorophospahte).

Water

Water is commonly used as a carrier material in oral care compositions due to its many benefits. For example, water is useful as a processing aid, is benign to the oral cavity and assists in quick foaming of toothpastes. Water may be added as an ingredient in its own right or it may be present as a carrier in other common raw materials such as, for example, sorbitol and sodium lauryl sulfate.

In some aspects, the oral care compositions herein may include from about 3% to about 70%, preferably from about 5% to about 30%, preferably from about 5% to about 30%, by weight of the composition, of total water content. The term "total water content" as used herein means the total amount of water present in the oral care composition, whether added separately or as a solvent or carrier for other raw materials but excluding that which may be present as water of crystallization in certain inorganic salts. Preferably, the water is USP water.

Alternatively, in other aspects, the oral care compositions herein may include from 0% to about 5%, by weight of the composition, of total water content. For example, the oral care composition may be substantially free of water, preferably free of water.

Surfactants

Optionally, but preferably, the oral care compositions comprise a surfactant. The surfactant may be selected from anionic, nonionic, amphoteric, zwitterionic, cationic surfactants, or combinations thereof, preferably the surfactant is anionic, more preferably the anionic surfactant is sodium lauryl sulfate (SLS). An example of a zwitterionic surfactant is cocamidopropyl betaine. The oral care composition may contain one, two, or more surfactants. In one aspect, the surfactant is selected from the group consisting of sodium lauryl sulfate, cocamidopropyl betaine, and mixtures thereof. The composition may include surfactant at a level of from about 0.1% to about 20%, preferably from about 1% to about 10%, by weight of the total composition.

Humectants

The oral care compositions herein may include humectants present in the amount of from 0% to about 70%, or from about 15% to about 55%, by weight of the composition. Humectants keep oral care compositions from hardening upon exposure to air and certain humectants may also impart desirable sweetness of flavor to oral care compositions. Suitable examples of humectants may include glycerin, sorbitol, polyethylene glycol, propylene glycol, xylitol, trimethyl glycine, and mixtures thereof. Other examples may include other edible polyhydric alcohols. In some aspects, the humectant is selected from sorbitol, glycerin, and combinations thereof. Preferably the humectant is sorbitol. In an aspect, the composition comprises from about 1% to about 60%, alternatively from about 30% to about 55%, of humectant by weight of the composition.

Abrasives

The oral care composition comprises an effective amount of an abrasive. Examples of abrasives include a calcium-containing abrasive, a sodium-containing abrasive, a silica, or combinations thereof. If containing a calcium-containing abrasive, the calcium-containing abrasive is preferably selected from the group consisting of calcium carbonate, dicalcium phosphate, tricalcium phosphate, calcium orthophosphate, calcium metaphosphate, calcium polyphosphate, calcium oxyapatite, and combinations thereof. If containing a sodium-containing abrasive, the sodium-containing abrasive is preferably selected from the group consisting of sodium carbonate, sodium bicarbonate, and combinations thereof. If a silica, preferably the silica is a precipitated silica (e.g., sodium silicate solution by destabilizing with acid as to yield very fine particles) such as those from the ZEODENT® series from Huber Engineered Materials (e.g., ZEODENT® 103, 124, 113 115, 163, 165, 167). It is acknowledged that some of these silicas (e.g., synthetic amorphous silica) can perform both abrasive and thickening functions, but are included herein under the term "abrasive" for purposes of the present invention. Preferably the oral care composition comprises from about 1% to about 35%, more preferably from about 5% to about 25%, by weight of the composition, of abrasive.

Flavoring Agent

The oral care composition herein may include from about 0.01% to about 5%, preferably from about 0.1% to about 2%, by weight of the composition, of a flavoring agent. Examples of suitable flavoring agent that may be used in the oral care composition include those described in U.S. Pat. No. 8,691,190 (Haught, J. C.) from column 7, line 61 to column 8, line 21. In some aspects, the flavoring agent may comprise methyl salicylcate, menthol, eugenol, cineol, or mixtures thereof. In some aspects, the oral care composition may comprise a flavoring agent which is free of, or substantially free of, methyl salicylcate, menthol, eugenol, and/or cineol.

Sweetener

The oral care compositions herein may include a sweetening agent. The sweetening agent is generally present in the oral care compositions at levels of from about 0.005% to about 5%, by weight of the composition. Suitable examples of sweetener include saccharin, dextrose, sucrose, lactose, xylitol, maltose, levulose, aspartame, sodium cyclamate, D-tryptophan, dihydrochalcones, acesulfame, sucralose, neotame, and mixtures thereof. Other suitable examples of sweetener are described in U.S. Pat. No. 8,691,190 (Haught, J. C.) from column 9, line 18 to column 10, line 18.

Coloring Agents

The oral care compositions herein may include a coloring agent present in the amount of from about 0.001% to about 5%, preferably from about 0.1% to about 1%, by weight of the composition. The coloring agent may be in the form of an aqueous solution, preferably 1% coloring agent in a solution of water. Suitable examples of coloring agents may include pigments, pealing agents, filler powders, talc, mica, magnesium carbonate, calcium carbonate, bismuth oxychloride, zinc oxide, and other materials capable of creating a visual change to the oral care compositions. Other suitable examples may include titanium dioxide ($TiO_2$). Titanium dioxide is a white powder which adds opacity to the compositions and is generally present in the oral care compositions at levels of from about 0.25% to about 5%, by weight of the composition.

Other Ingredients

The present oral care composition can comprise the usual and conventional ancillary components that are known to one skilled in the art. Optional ingredients include, for example, but are not limited to, anti-plaque agent, anti-sensitivity agent, whitening and oxidizing agent, anti-inflammatory agent, anti-calculus agent, chelating agent, tooth substantive agent, analgesic and anesthetic agent. It will be appreciated that selected components for the oral care compositions must be chemically and physically compatible with one another.

Method of Use

In one aspect, the present invention relates to a method for cleaning or polishing teeth in a subject. The method of cleaning or polishing herein comprises contacting a subject's teeth with the oral care compositions according to the present invention.

In another aspect, the present invention relates to a method of inhibiting biofilm formation or disrupting biofilm in an oral cavity (e.g. on a tooth) comprising administering to the oral cavity (e.g. the tooth) an oral care composition according to the present invention, wherein preferably the administering occurs at least once a day, more preferably at least twice a day.

In another aspect, the present invention also relates to a method of promoting Gum Health in a subject comprising administering to the subject's oral cavity an oral care composition according to the present invention, wherein preferably the administering occurs at least once a day, more preferably at least twice a day.

In yet another aspect, the present invention also relates to a method of promoting Gum Health, wherein promoting Gum Health comprises:

(i) improving gingival wound healing in the oral cavity; and (ii) improve reduction of bacterial activity in the oral cavity.

The methods as described above may be by brushing (e.g., toothbrushing) with an oral care composition (e.g., dentifrice) or rinsing with an oral care composition (e.g., dentifrice slurry or mouth rinse). The oral care compositions may be applied neat or via a delivery apparatus such as, for example, a toothbrush. Other methods include contacting the topical oral gel, mouth spray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral care composition may be used as frequently as toothpaste, or may be used less often, for example, weekly, or used by a professional in the form of a prophy paste or other intensive treatment.

Test Method: Assay for Measuring Biofilm Architecture, Penetration of Anti-Bacterial Agent & Endotoxin Neutralization in the Biofilms The following assay is used an in situ plaque biofilm for inventive oral care compositions of the present invention in order to determine:

1—penetration efficiency of stannous ions with bacteria via measurement of co-localization percentage.

2—improved endotoxin neutralization of anti-bacterial agent in the biofilms via LPS binding efficiency of stannous ions via measurement of a fluorescent dye that is bound to lipid A of LPS.

Details of the assay are described below.

(a) Substrate for Biofilm Growth

Hydroxyapatite ("HA") disks are used for in situ growth of biofilms. The HA disks are designed having three parallel grooves (i.e., 200 µm wide; 200 µm deep for two sides' grooves; while 500 µm wide and 500 µm deep for the middle groove) in each disk. When attaching disks to subject's mouth, keep these grooves vertical, to mimic interproximal gap between teeth, which is the hard-to-clean area where plaque generally tends to accumulate. This model allows the collection of undisturbed plaque from the grooves. HA disks are manufactured by Shanghai Bei'erkang biomedicine limited company (Shanghai, China).

(b) Wearing the Splint

Figure 2:
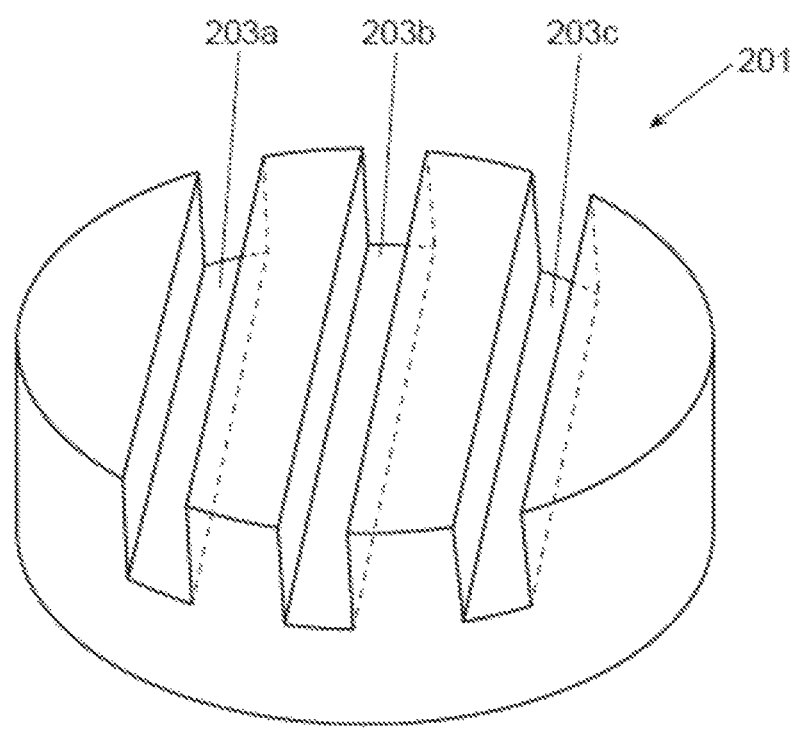
FIG. 2 is a perspective view of the HA disk having grooves therein.
Figure 3:
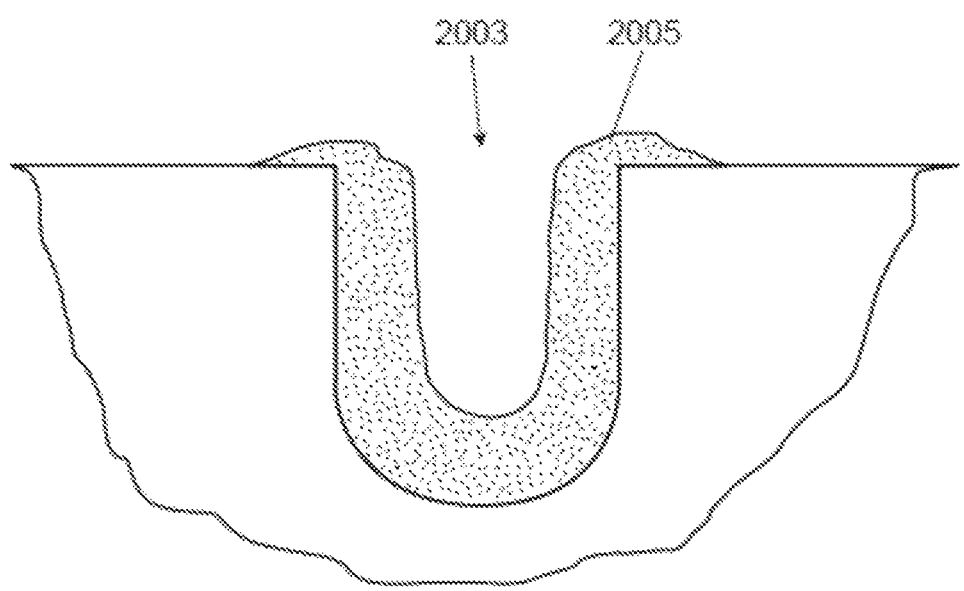
FIG. 3 is a schematic of a cross sectional view of the groove with biofilm therein.

Human subjects wear the splint. Each subject wears up to 12 HA disks on the splint to ensure that, at least, 9 HA disks are available after 48 hours. A non-limiting example of such a splint and HA disks are shown in FIG. 1. With reference to FIG. 1, the device (1) holds a plurality of HA disks (2a-2d). In a specific example, and with reference to FIG. 2, the HA disk (201) has three parallel grooves (203) (the two sides' grooves (203a and 203c) are 300 µm wide and 300 µm deep; while the middle grove (203b) (in between the two side grooves) is 500 µm wide and 500 µm deep). The middle groove is designed wider and deeper than the two sides' grooves so that the HA disk can be more easily separated into two identical half-disks for head-to-head comparison purposes. FIG. 3 is a schematic of a cross-sectional view of the groove (2003) with biofilm (2005) therein. Further details of the HA disks are described in US2017/0056531 (e.g. paragraphs [0019]-[0020]).

Although not shown in FIG. 3, the disks can be positioned such that the recede is in the inter-dental space between the teeth (since this location is prone to plaque (given the difficulty in cleaning, etc.) The subjects withdraw the splint only during meals (the splint stored in an opaque container in humid conditions) and to perform oral hygiene procedures Immediately thereafter, the splint is worn again. Subjects are asked to use a straw when drinking.

(c) In-Situ Biofilms Release from HA Desk

All HA disks are removed from the splint at 48 hours by tweezers. Tweezers are used to hold the edge of HA chips and transfer the HA disk to a 2 mL centrifuge tube containing PBS (phosphate buffered saline) solution. Tweezers are washed thoroughly (water; 75% alcohol; and then deionized water) before every disk transfer.

(d) Preparation of Toothpaste Supernatant 15 grams of deionized water is added to 5 grams toothpaste (using any one of the Examples 1-5). After stirring thoroughly, the mixture is centrifuge at 12,000 RPM for 20 minutes. The supernatant is prepared one day before usage and stored at 4° C.

(e) Confocal Laser Scanning Microscopy

After the HA disks are removed from the splint. The HA disks are used for ex vivo treatment by the different inventive and comparative compositions. After being treated with the subject supernatant and labeled with microbial fluorescent probe and stannous fluorescent probe (such as described in US2018/0072944A1; Shi et al.), the biofilms in the grooves are measured by confocal laser scanning microscopy ("CLSM") (as described below).

(f) Disk Preparation

The HA disks are rinsed in PBS solution and each HA disk is divided into two halves by tweezers. Thereafter, each half-disk is placed into 500-1000 µL of PBS solution statically for 1 minute. Each disk is treated for two minutes by either PBS solution or toothpaste supernatant. Each disk is washed by holding each disk with tweezers, shaken for ten rounds of back and forth in 1 mL of PBS solution, and then this washing cycle is repeated. Then each disk is immersed into 500-1000 µL PBS solution statically for 5 minutes.

After being treated with PBS and/or the oral care composition (e.g., toothpaste) supernatant and labeled with specific fluorescent probes, the biofilm in the grooves is measured by confocal laser scanning microscopy (CLSM).

(g) Fluorescence Probe Staining and Microscopy

"Ion fluorescent probe" means a fluorescent probe that specifically binds to one kind of ions and emit fluorescence at a certain wavelength. In recent years, significant emphasis has been placed on the development of new, highly selective fluorescent probes of ions because of their potential applications in biochemistry and environmental research. Many kinds of signaling mechanisms have been proposed and utilized for optical detection of ions, including photo-induced electron/energy transfer (PET), intramolecular charge transfer (ICT), fluorescence resonance energy transfer (FRET), and so on. Some of these fluorescent probes can also be applied in fluorescence bioimaging, which causes little cell damage and is highly sensitive with high-speed spatial analysis of living cells. Specifically, FRET imaging that affords simultaneous recording of two emission intensities at different wavelengths in the presence and absence of analytes has provided a facile method for visualizing complex biological processes at the molecular level. This technique appears to be suited to the study of physiological functions or pathogenesis of ions in biofilm and human body.

Stannous penetration efficiency of stannous ions with bacteria via measurement of co-localization percentage. Non-limiting examples of a stannous fluorescent probe suitable for labeling the biofilm may include any one following of the compounds: (a) tert-butyl (3',6'-diamino-3-oxospiro[isoindoline-1,9'-xanthen]-2-yl)carbamate; (b) tert-butyl (3',6'-bis(dimethylamino)-3-oxospiro[isoindoline-1,9'-xanthen]-2-yl)carbamate; (c) tert-butyl (3',6'-bis(diethylamino)-3-oxospiro[isoindoline-1,9'-xanthen]-2-yl) carbamate; (d) tert-butyl (3',6'-bis(ethylamino)-2',7'-dimethyl-3-oxospiro[isoindoline-1,9'-xanthen]-2-yl) carbamate; (e) tert-butyl (3',6'-diamino-2',7'-dimethyl-3-oxospiro[isoindoline-1,9'-xanthen]-2-yl)carbamate; (f) tert-butyl (3-oxo-3',6'-di(pyrrolidin-1-yl)spiro[isoindoline-1,9'-xanthen]-2-yl)carbamate; (g) tert-butyl (3-oxo-3',6'-bis(phenylamino)spiro[isoindoline-1,9'-xanthen]-2-yl) carbamate; (h) tert-butyl (3-oxo-3',6'-di(piperidin-1-yl)spiro[isoindoline-1,9'-xanthen]-2-yl)carbamate; (i) tert-butyl (3',6'-dimorpholino-3-oxospiro[isoindoline-1,9'-xanthen]-2-yl) carbamate; (j) tert-butyl(2',7'-dibutyl-3',6'-bis(diethylamino)-3-oxospiro[isoindoline-1,9'-xanthen]-2-yl) carbamate; (k) tert-butyl (2',7'-dimethyl-3-oxo-3',6'-di(piperidin-1-yl)spiro[isoindoline-1,9'-xanthen]-2-yl) carbamate; (l) tert-butyl (3-oxo-1',2',3',4',10',11',12',13'-octahydrospiro[isoindoline-1,7'-pyrano[2,3-f:6,5-f'] diquinolin]-2-yl)carbamate; (m) tert-butyl (3-oxo-1',2',3',4',8',9',10',11'-octahydrospiro[isoindoline-1,6'-pyrano[3,2-g:5,6-g']diquinolin]-2-yl)carbamate; (n) N-(3',6'-bis(diethylamino)-3-oxospiro[isoindoline-1,9'-xanthen]-2-yl) propionamide; (p) N-(3',6'-bis(diethylamino)-3-oxospiro[isoindoline-1,9'-xanthen]-2-yl)butyramide; and (q) N-(3',6'-bis(diethylamino)-3-oxospiro[isoindoline-1,9'-xanthen]-2-yl)pentanamide. Preferably the stannous probe is selected from: N-(3',6'-bis(diethylamino)-3-oxospiro[isoindoline-1,9'-xanthen]-2-yl)propionamide; N-(3',6'-bis(diethylamino)-3-oxospiro[isoindoline-1,9'-xanthen]-2-yl)butyramide; and N-(3',6'-bis(diethylamino)-3-oxospiro[isoindoline-1,9'-xanthen]-2-yl)pentanamide.

Generally, these stannous fluorescent probes contain a Rhodamine B derivative moiety as fluorophore, linked via amide moiety to a carbazate group. Further details are described in the WO 2015/139577 A1 (24 Sep. 2015) or US equivalent publication thereof. Preferably, the stannous fluorescent probe is tert-butoxy-carboxamide,N-[3',6'-bis(diethylamino)-3-oxospiro[1H-isoindole-1,9'-[9H]xanthen]-H)-yl]

The "Microbial fluorescent probe" means a fluorescent probe that binds to microbes of a biofilm and emit fluorescence at a certain wavelength. One class of such probes includes fluorescently labeled oligonucleotides, preferably rRNA-directed oligonucleotides. Non-limiting examples include SYTO™ branded dyes. One specific example is SYTO® 9 Green Fluorescent Nucleic Acid Stain, wherein excitation is a 485 (DNA) and 486 (RNA), and light emission is detected at 498 (DNA) and 501 (RNA).

After treatment and immersing, each half-disk is stained with the Sn probe together with Syto-9 probe (containing 5 µM Syto-9 and 5 µM Sn probe) for 30 minutes in the dark. The SYTO-9/Sn dye stained samples, the following parameters are used: $\lambda ex=488$ nm/560 nm, $\lambda em=500/580$ nm, 20× objective lens, and scanning from bottom of surface bacteria for 60 µm with step size=3 µm.

The LPS neutralization effect was evaluated using BODIPY-TR-cadaverine (BC), a fluorescent dye that is bound to lipid A, thereby suppressing its fluorescence. BC is displaced by agents with an affinity for this lipid. When LPS are bound by other ions, e.g., stannous, BC is released from the LPS and its fluorescence is proportional to the amount of free (unbound) BC present. Therefore, the level of fluorescence indicates the amount of neutralized (bound) LPS versus free (unbound) LPS, and the efficacy of an antibacterial agent in reducing the biofilm's toxicity. The greater the amount of bound LPS, the lower its toxicity.

After treatment and immersing, each half-disk is stained with the BODIPY-TR-cadaverine (BC) probe together with Syto-9 probe (containing 5 µM Syto-9 probe and 5 µM BC probe) for 30 minutes in the dark. After staining, each disk is immersed into 500-1000 µL PBS solution statically for 2 minutes. The disks are washed again, by holding each disk with tweezers, shaken for five rounds of back and forth in 1 mL PBS solution, and repeated. For SYTO-9/BC dye stained samples, the following parameters are used: $\lambda ex=488$ nm/588 nm, $\lambda em=500/616$ nm, 20× objective lens, and scanning from bottom of surface bacteria for 60 µm with step size=3 µm.

(h) Confocal Laser Scanning Microscopy

The Leica™ TCS SP8 AOBS spectral confocal microscope is used. The confocal system consists of a Leica™ DM6000B upright microscope and a Leica™ DMIRE2 inverted microscope. An upright stand is used for applications involving slide-mounted specimens; whereas the inverted stand, having a 37° C. incubation chamber and $CO_2$ enrichment accessories, provides for live cell applications. The microscopes share an exchangeable laser scan head and, in addition to their own electromotor-driven stages, a galvanometer-driven high precision Z-stage which facilitates rapid imaging in the focal (Z) plane. In addition to epifluorescence, the microscopes support a variety of transmitted light contrast methods including bright field, polarizing light and differential interference contrast, and are equipped with 5×, 20×, 40×, 63× (oil and dry) and 100× (oil) Leica™ objective lenses.

The laser scanning and detection system is described. The TCS SP8 AOBS confocal system is supplied with four lasers (one diode, one argon, and two helium neon lasers) thus allowing excitation of a broad range of fluorochromes within the UV, visible and far red ranges of the electromagnetic spectrum. The design of the laser scan head, which incorporates acousto-optical tunable filters ("AOTF"), an acousto-optical beam splitter ("AOBS") and four prism spectrophotometer detectors, permits simultaneous excitation and detection of three fluorochromes. The upright microscope also has a transmission light detector making it possible to overlay a transmitted light image upon a fluorescence recording.

Leica™ Confocal software LAS AF3.3.0 is used. The confocal is controlled via a standard Pentium PC equipped with dual monitors and running Leica™ Confocal Software. The Leica Confocal Software LAS AF3.3.0 (available from Leica Lasertechnik GmbH, Heidelberg, Germany) provides an interface for multi-dimensional image series acquisition, processing and analysis, that includes 3D reconstruction and measurement, physiological recording and analysis, time-lapse, fluorochrome co-localization, photo-bleaching techniques such as FRAP and FRET, spectral immixing, and multicolour restoration.

(i) Image Analysis

Sn Analysis; The SYTO-9/Sn dye stained samples are chosen to quantify overlap efficiency of red and green pixels. Using the software, the pixel overlap of "green" bacterial probes and that of "red" stannous probes are identified, and then this value is divided by all non-black pixels (that include non-overlapping stannous probes) to provide a co-localization percentage of stannous in bacteria. Generally, the higher this co-localization percentage, the more efficacious the oral care product is in delivering stannous into bacteria. (See Xiang J, Li H, Pan B, Chang J, He Y, He T, Strand R, Shi Y, Dong W. (2018) Penetration and Bactericidal Efficacy of Two Oral Care Products in an Oral Biofilm Model. *Am J Dent*, Vol. 31, Issue 1: 53-60).

LPS Analysis; The SYTO-9/BC probe stained samples are chosen to quantify fluorescence intensity of red and green pixels. Using the software, the fluorescence intensity ratio (FIR) of bound LPS/bacterial cell was calculated. This ratio of fluorescence intensity indicates the relative amount of bound (neutralized) LPS per unit of bacteria, and the efficacy of an agent in reducing the biofilm's toxicity. The greater the fluorescence intensity ratio, the higher LPS endotoxin neutralization efficacy.

EXAMPLES

The following are non-limiting examples of oral care compositions of the present invention, as well as comparative examples.

TABLE 1

Compositions

| Ingredients | Ex. 1 (comparative) | Ex. 2 | Ex. 3 | Ex. 4 (comparative) | Ex. 5 | Ex. 6 | Ex. 7 |
|---|---|---|---|---|---|---|---|
| Humectants (sorbitol, glycerin, propylene glycol, and/or polyethlylene glycol) | 42.500 | 40.500 | 38.500 | 48.500 | 46.500 | 65.000 | 48.000 |
| Sodium Hexametaphosphate | 13.000 | 13.000 | 13.000 | — | — | — | — |
| Tetrasodium Pyrophosphate | — | — | — | 2.000 | 2.000 | — | — |
| Sodium tripolyphosphate | — | — | — | — | — | 5.000 | — |
| Phytic Acid | — | — | — | — | — | — | 0.800 |
| Stannous Fluoride | 0.454 | 0.454 | 0.454 | 0.454 | 0.454 | 0.454 | — |
| Stannous Chloride | — | — | — | — | — | — | 1.160 |
| Sodium Fluoride | — | — | — | — | — | — | 0.321 |
| Zinc Lactate Dihydrate | 1.900 | 1.900 | 1.900 | — | — | — | — |
| Zinc Phosphate | — | — | — | 1.000 | 1.000 | — | — |
| Zinc Citrate | — | — | — | — | — | — | 0.533 |
| Glycine | — | 2.000 | 4.000 | — | 2.000 | 2.000 | 2.000 |
| Sodium Gluconate | 0.625 | 0.625 | 0.625 | — | — | — | 1.300 |
| Buffering & pH Agents (sodium citrate, citric acid, and/or trisodium phosphate dodecahydrate) | 1.100 | 1.100 | 1.100 | 1.200 | 1.200 | 1.100 | 1.100 |
| Thickeners (xanthan gum, carrageenan, sodium carboyxmethyl cellulose, and/or polyacrylic acid polymer) | 0.850 | 0.850 | 1.850 | 1.500 | 1.500 | 1.300 | 2.375 |
| Silica Abrasive | 25.000 | 25.000 | 25.000 | 20.000 | 20.000 | 17.000 | 20.000 |
| Sodium Lauryl Sulfate (28% soln.) | 3.400 | 3.400 | 3.400 | 5.500 | 5.500 | 3.500 | 6.500 |

TABLE 1-continued

Compositions

| Ingredients | Ex. 1 (comparative) | Ex. 2 | Ex. 3 | Ex. 4 (comparative) | Ex. 5 | Ex. 6 | Ex. 7 |
|---|---|---|---|---|---|---|---|
| Cocamidopropyl Betaine | — | — | — | 0.500 | 0.500 | 0.500 | 2.000 |
| Flavor & Sweetener | 1.100 | 1.100 | 1.100 | 1.100 | 1.100 | 1.100 | 1.100 |
| Water and minors (e.g., colorant) | qs | qs | qs | qs | qs | qs | qs |
| Total | 100% | 100% | 100% | 100% | 100% | 100% | 1000% |
| Concentration of Phosphate Ion (mMol) | 60 | 60 | 60 | 50 | 50 | 130 | 12 |

The following table provides data regarding stannous penetration and LPS neutralization (according to the test method described above) for certain oral care compositions.

TABLE 2

Sn Penetration and LPS Neutralization

| Product | Sn Penetration Efficiency (%) | LPS Neutralization Efficiency (Ratio BODIPY TR: Cell) |
|---|---|---|
| Example 1 (comparative) | 76.49 | 1.38 |
| Example 2 | 91.41 | 1.62 |
| Example 4 (comparative) | 69.28 | 1.15 |
| Example 5 | 88.60 | 1.50 |

The data shows the benefits of adding a suitable neutral amino acid, such as glycine, with stannous and polyphosphates salts to increase the stannous penetration and the resultant bacterial LPS neutralization within the biofilm. Ex. 1 shown in TABLE 1, is a comparative composition that includes stannous fluoride and sodium hexametaphosphate. The use of Ex. 1 led to a final Sn penetration of 76.49%, and a LPS neutralization ratio (BODIPY TR:Cell) of 1.38. Ex. 2 is a toothpaste composition, as shown in TABLE 1, with stannous fluoride, polyphosphate and glycine at 2 wt. %. The use of Ex. 2 led to a final Sn penetration of 91.41%, and a LPS neutralization ratio (BODIPY TR:Cell) of 1.62. Unexpectedly, the addition of 2% glycine between Ex. 1 and Ex. 2, led to a 20% improvement in Sn penetration and a 17% improvement in LPS neutralization. Ex. 4 shown in TABLE 1, is a comparative composition that includes stannous fluoride and tetrasodium pyrophosphate. The use of Ex. 4 led to a final Sn penetration of 69.28%, and a LPS neutralization ratio (BODIPY TR:Cell) of 1.15. Ex. 5 is a toothpaste composition, as shown in TABLE 1, with stannous fluoride, tetrasodium pyrophosphate and glycine at 2 wt. %. The use of Ex. 5 led to a final Sn penetration of 88.60%, and a LPS neutralization ratio (BODIPY TR:Cell) of 1.50. Unexpectedly, the addition of 2% glycine between Ex. 4 and Ex. 5, led to a 28% improvement in Sn penetration, and a 30% improvement in LPS neutralization.

Comparisons were made pairwise using One-way ANOVA and Student-Neuman-Keuls test, and $P<0.05$ was considered statistically significant in showing the benefits of adding glycine to stannous and polyphosphate compositions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a) from about 0.01% to about 5%, by weight of the composition, of a stannous ion source, wherein the stannous ion source comprises stannous fluoride, stannous chloride, or combinations thereof;
   b) from about 0.01% to about 10%, by weight of the composition, of a neutral amino acid, wherein the neutral amino acid comprise glycine; and
   c) polyphosphate, wherein the polyphosphate comprises pyrophosphate, tripolyphosphate, hexametaphosphate, or combinations thereof;
   wherein the concentration of phosphate ion is greater than about 10 mMol.

2. The oral care composition of claim 1, wherein the oral care composition has a pH of from 5 to 10.

3. The oral care composition of claim 1, wherein the concentration of phosphate ion is from about 10 mMol to about 200 mMol.

4. The oral care composition of claim 3, wherein the concentration of phosphate ion is from about 10 mMol to about 150 mMol.

5. The oral care composition of claim 1, wherein the neutral amino acid is present in an amount of from about 0.05% to about 5%, by weight of the composition.

6. The oral care composition of claim 5, wherein the neutral amino acid is present in an amount of from about 1% to about 3%, by weight of the composition.

7. The oral care composition of claim 1, wherein the stannous ion source is present in an amount of from about 0.05% to about 4%, by weight of the composition.

8. The oral care composition of claim 7, wherein the stannous ion source is present in an amount of from about 0.1% to about 2%, by weight of the composition.

9. The oral care composition of claim 1, wherein the oral care composition comprises from about 0.1% to about 25%, by weight of the composition, of polyphosphate.

10. The oral care composition of claim 1, wherein the oral care composition comprises less than 12.75%, by weight of the composition, of polyphosphate.

11. The oral care composition of claim 1, wherein the oral care composition comprises greater than 13.25%, by weight of the composition, of polyphosphate.

12. The oral care composition of claim 1, wherein the oral care composition further comprises from about 0.1% to about 5%, by weight of the composition, of a zinc ion source.

13. The oral care composition of claim 12, wherein the oral care composition comprises from about 0.2% to about 2%, by weight of the composition, of the zinc ion source.

14. The oral care composition of claim 12, wherein the zinc ion source is selected from the group consisting of zinc citrate, zinc chloride, zinc sulfate, zinc gluconate, zinc lactate, zinc phosphate, zinc oxide, zinc carbonate, and mixtures thereof.

15. The oral care composition of claim 14, wherein the zinc ion source is selected from the group consisting of zinc citrate, zinc gluconate, zinc lactate, and mixtures thereof.

16. The oral care composition of claim 1, wherein the oral care composition further comprises from about 0.0025% to about 10%, by weight of the composition, of a fluoride ion source.

17. The oral care composition of claim 16, wherein the oral care composition comprises from about 0.05% to about 4%, by weight of the composition, of the fluoride ion source.

18. The oral care composition of claim 16, wherein the fluoride ion source is selected from the group consisting of sodium fluoride, stannous fluoride, potassium fluoride, sodium monofluorophosphate, indium fluoride, amine fluoride, zinc fluoride, and mixtures thereof.

19. The oral care composition of claim 1, wherein the oral care composition further comprises from about 0.01% to 10%, by weight of the composition, of a thickening agent, wherein the thickening agent is selected from a thickening polymer, a thickening silica, or mixtures thereof.

20. The oral care composition of claim 1, wherein the oral care composition further comprises from about 1% to about 35%, by weight of the composition, of an abrasive.

21. The oral care composition of claim 20, wherein the oral care composition comprises from about 5% to about 25%, by weight of the composition, of abrasive.

22. The oral care composition of claim 20, wherein the abrasive is selected from a calcium-containing abrasive, a sodium-containing abrasive, a silica abrasive, or mixtures thereof.

23. The oral care composition of claim 22, wherein the abrasive is a silica abrasive.

24. The oral care composition of claim 1, wherein the oral care composition further comprises from about 1% to about 60%, by weight of the composition, of a humectant.

25. The oral care composition of claim 24, wherein the oral care composition comprises from about 30% to about 55%, by weight of the composition, of humectant.

26. The oral care composition of claim 24, wherein the humectant is a polyol selected from sorbitol, glycerin, or mixtures thereof.

27. The oral care composition of claim 1, wherein the composition has a pH of from about 4.5 to about 11.

28. The oral care composition of claim 27, wherein the composition has a pH of from about 5 to about 10.

29. A method of inhibiting biofilm formation or disrupting biofilm in an oral cavity comprising administering to the oral cavity an oral care composition according to claim 1.

30. The method of claim 29, wherein the administering occurs at least once a day.

31. The method of claim 29, wherein the administering occurs at least twice a day.

* * * * *

UNITED STATES PATENT AND TRADEMARK OFFICE
CERTIFICATE OF CORRECTION

PATENT NO. : 11,419,799 B2
APPLICATION NO. : 17/035863
DATED : August 23, 2022
INVENTOR(S) : Ross Strand and Yunming Shi It is certified that error appears in the above-identified patent and that said Letters Patent is hereby corrected as shown below:

On the Title Page

Before Item (51) Int. Cl., please insert the following paragraphs:
-- (30) Foreign Application Priority Data
Sep. 30, 2019 (CN) PCT/CN2019/109425 --

Signed and Sealed this
Sixth Day of December, 2022

Katherine Kelly Vidal
*Director of the United States Patent and Trademark Office*